United States Patent

Zhu et al.

[11] Patent Number: 5,843,136
[45] Date of Patent: Dec. 1, 1998

[54] PACING OUTPUT CIRCUITRY FOR AUTOMATIC CAPTURE THRESHOLD DETECTION IN CARDIAC PACING SYSTEMS

[75] Inventors: Qingsheng Zhu, Little Canada; Julio C. Spinelli, Shoreview, both of Minn.

[73] Assignee: Cardiac Pacemakers, Inc., St. Paul, Minn.

[21] Appl. No.: 977,272

[22] Filed: Nov. 24, 1997

[51] Int. Cl.$^6$ ............................................. A61N 1/39
[52] U.S. Cl. ................................. 607/13; 607/28
[58] Field of Search ................... 607/13, 9, 28

[56] References Cited

U.S. PATENT DOCUMENTS

| | | |
|---|---|---|
| 4,373,531 | 2/1983 | Wittkampf et al. . |
| 4,399,818 | 8/1983 | Money . |
| 4,537,201 | 8/1985 | Delle-Vedove et al. . |
| 4,674,508 | 6/1987 | DeCote . |
| 4,686,988 | 8/1987 | Sholder . |
| 4,821,724 | 4/1989 | Whigham et al. . |
| 4,858,610 | 8/1989 | Callaghan et al. . |
| 5,324,310 | 6/1994 | Greeninger et al. . |
| 5,486,201 | 1/1996 | Canfield . |

*Primary Examiner*—Scott M. Getzow
*Attorney, Agent, or Firm*—Haugen and Nikolai, P.A.

[57] ABSTRACT

A method and apparatus for attenuating polarization voltages or "afterpotentials" which develop at the heart tissue/electrode interface following the delivery of a pacing stimulus to the heart tissue such that the evoked response of the heart may be accurately detected to determine whether each pacing stimulus resulted in heart capture or contraction, thereby facilitating improved tracking of the capture threshold for minimizing power consumption while assuring therapeutic efficacy. The conventional large capacitance coupling capacitor used to suppress DC components of the pacing spike has a second, much lower capacitance capacitor connector in series with it, the second capacitor being shunted by a switch so that its value can be selectively inserted in series with the coupling capacitor to effectively lower the overall capacitance of the coupling capacitor following delivery of the pacing spike.

9 Claims, 3 Drawing Sheets

PACING OUTPUT CIRCUITRY FOR AUTOMATIC CAPTURE THRESHOLD DETECTION IN CARDIAC PACING SYSTEMS

BACKGROUND OF THE INVENTION

I. Field of the Invention

The present invention relates generally to the field of cardiac pacemakers, including atrial, ventricular, and dual chamber pacemakers. More specifically, the present invention relates to a method and apparatus for attenuating polarization voltages or "afterpotentials" which develop at the heart tissue/electrode interface following the delivery of a pacing stimulus to the heart tissue such that the evoked response of the heart may be accurately detected to determine whether each pacing stimulus resulted in heart capture or contraction, thereby facilitating improved tracking of the capture threshold for minimizing power consumption while assuring therapeutic efficacy.

II. Discussion of the Prior Art

Cardiac pacemakers have enjoyed widespread use and popularity through time as a means for supplanting some or all of an abnormal heart's natural pacing functions. Among the various heart abnormalities remedied by pacemakers include total or partial heart block, arrhythmias, myocardial infarctions, congestive heart failure, congenital heart disorders, and various other rhythm disturbances within the heart. The fundamental components of a cardiac pacemaker include an electronic pulse generator for delivering stimulus pulses to the heart and an electrode lead arrangement (unipolar or bipolar) for sensing evoked responses from the heart. Cardiac pacemakers may be categorized generally as either external or implantable. External cardiac pacemakers are characterized as having the electronic pulse generator which resides outside the body with one or more electrode leads passing through the skin and ultimately into the heart for delivering pacing stimulus pulses and sensing evoked responses. Such external pacemakers are typically employed for temporary pacing, such as following a heart attack or open heart surgery, and are removed when no longer needed. Implantable pacemakers are used for long-term pacing and are characterized as having both the electrical pulse generator and electrode lead arrangement surgically implanted within the body of the patient. Depending upon the heart abnormality, cardiac pacemakers may be designed to engage in ventricular pacing, atrial pacing, or dual chamber pacing in both the atrium and ventricle.

Regardless of which type of cardiac pacemaker is employed to restore the heart's natural rhythm, all operate to stimulate excitable heart tissue cells adjacent to the electrode of the pacing lead employed with the pacemaker. Myocardial stimulation or "capture" is a function of the positive and negative charges found in each myocardial cell within the heart. More specifically, the selective permeability of each myocardial cell works to retain potassium and exclude sodium such that, when the cell is at rest, the concentration of sodium ions outside of the cell membrane is approximately equal to the concentration of potassium ions inside the cell membrane. However, the selective permeability also retains other negative particles within the cell membrane such that the inside of the cell membrane is negatively charged with respect to the outside when the cell is at rest. When a stimulus is applied to the cell membrane, the selective permeability of the cell membrane is disturbed and it can no longer block the inflow of sodium ions from outside the cell membrane. The inflow of sodium ions at the stimulation site causes the adjacent portions of the cell membrane to lose its selective permeability, thereby causing a chain reaction across the cell membrane until the cell interior is flooded with sodium ions. This process, referred to as depolarization, causes the myocardial cell to have a net positive charge due to the inflow of sodium ions. The electrical depolarization of the cell interior causes a mechanical contraction or shortening of the myofibrils of the cell membrane. The syncytial structure of the myocardium will cause the depolarization originating in any one cell to radiate through the entire mass of the heart muscle so that all cells are stimulated for effective pumping. Following heart contraction or systole, the selective permeability of the cell membrane returns and sodium is pumped out until the cell is repolarized with a negative charge within the cell membrane. This causes the cell membrane to relax and return to the fully extended state, referred to as diastole.

In a normal heart, the sino-atrial (SA) node initiates the myocardial stimulation or "capture" sequence described above. The SA node comprises a bundle of unique cells disposed within the roof of the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole wherein the atria contract to empty blood into the ventricles. The atrial depolarization from the SA node is detected by the atrio-ventricular (AV) node which, in turn, communicates the depolarization impulse into the ventricles via the Bundle of His and Purkinje fibers following a brief conduction delay. In this fashion, ventricular systole lags behind atrial systole such that the blood from the ventricles is pumped through the body and lungs after being filled by the atria. Atrial and ventricular diastole follow wherein the myocardium is repolarized and the heart muscle relaxed in preparation for the next cardiac cycle. It is when this system fails or functions abnormally that a cardiac pacemaker may be needed to deliver an electronic pacing stimulus for selectively depolarizing the myocardium of the heart so as to maintain proper heart rate and synchronization of the filling and contraction of the atrial and ventricular chambers of the heart.

The success of a cardiac pacemaker in depolarizing or "capturing" the heart hinges on whether the energy of the pacing stimulus as delivered to the myocardium exceeds a threshold value. This threshold value, referred to as the capture threshold, represents the amount of electrical energy required to alter the permeability of the myocardial cells to thereby initiate cell depolarization. If the energy of the pacing stimulus does not exceed the capture threshold, then the permeability of the myocardial cells will not be altered and thus no depolarization will result. If, on the other hand, the energy of the pacing stimulus exceeds the capture threshold, then the permeability of the myocardial cells will be altered such that depolarization will result. Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at level higher than necessary to effect capture. This can be verified by lowering the stimulation energy level and monitoring for loss of capture at the new energy level. The ability to detect capture in a pacemaker is extremely desirable in that delivering stimulation pulses having energy far in excess of the patient's capture threshold is wasteful of the pacemaker's limited power supply. In order to minimize current drain on the power supply, it is desirable to automatically adjust the pacemaker such that the amount of stimulation energy delivered to the myocardium is maintained at the lowest level that will reliably capture the heart. To accomplish this, a process known as "capture verification" must be performed wherein the pacemaker monitors to determine whether an evoked depolarization or R-wave occurs in the heart following the delivery of each pacing stimulus pulse.

FIG. 1 is a circuit diagram illustrating a conventional pacing output circuit 10 found in any of a variety of prior art pacemakers. The pacing output circuit 10 is designed to selectively generate and deliver stimulus pulses to heart of a patient, indicated schematically as the resistive load 12, via a tip electrode 14 and ring electrode 16. The circuit 10 includes a power supply or battery 18, a first switch 20, a second switch 22, a third switch 24, a pacing charge storage capacitor 26, and a coupling capacitor 28, all of which cooperate operate under the direction of a microprocessor-based controller (not shown) to perform a charging cycle, a pacing cycle, and a recharging cycle. The charging cycle involves closing the first switch 20 and opening the second and third switches 22, 24 such that the pacing charge storage capacitor 26 is charged up to a predetermined voltage level. The pacing cycle involves opening the first and third switches 20, 24 and closing the second switch 22 such that the voltage within the pacing charge storage capacitor 26 may be discharged through the coupling capacitor 28 to the tip electrode 14 of the pacemaker. Immediately after pacing, the second and third switches 22, 24 are opened and the charges within the coupling capacitor 28 will decay slowly through leakage. The recharging cycle involves opening the first and second switches 20 and 22 and closing the third switch 24 for a predetermined period of time following the pacing pulse to allow the coupling capacitor 28 to be discharged through the load 12.

While the foregoing pacing circuit 10 is generally effective in delivering stimulus pulses to the heart 12, it has been found that the detection of evoked depolarization or "capture verification" is rendered very difficult due to polarization voltages or "afterpotentials" which develop at the heart tissue/electrode interface following the application of the stimulation pulses. The inventors in the present application have discovered that these polarization voltages are due, in large part, to the relatively large capacitance (e.g. 33 microfarads) of the coupling capacitor 28. The large capacitance of coupling capacitor 28 is required in order to sufficiently block any DC components from the heart 12. However, the large capacitance of the coupling capacitor 28 also causes a charge dissipation or "afterpotential" which is relatively large (100 mV or greater) and which decays exponentially over a relatively long period of time (100 mS). This is particularly troublesome due to the fact that the evoked potential or R-wave of the heart tissue is small in amplitude (5–20 mV) relative to the polarization voltage or "afterpotential" (100 mV). Moreover, the long decay period of the polarization voltage or "afterpotential" effectively masks the evoked potential or R-wave, which typically occurs within approximately (10–20) mS after the stimulation pulse. It will be appreciated that this creates difficulty in detecting the evoked response or R-wave of the heart following the delivery of stimulus pulses. In that evoked response is indicative of capture, the undesirable masking of the R-waves by "afterpotentials" thus hampers the ability of the pacemaker to conduct automatic capture verification.

The prior art is replete with patents which address the problem of polarization voltage or "afterpotentials" hindering capture verification in cardiac pacing systems. U.S. Pat. No. 4,373,531 to Wittkampf et al. teaches the use of pre and post stimulation recharge pulses to neutralize the polarization on the pacing lead. U.S. Pat. No. 4,399,818 to Money teaches the use of a direct-coupled output stage wherein polarization voltages at the heart tissue/electrode interface are dissipated by shorting the electrodes together. U.S. Pat. No. 4,498,478 to Bourgeois teaches the use of a resistor across the output terminals (electrodes) such that a current path is provided for discharging and recharging the effective capacitance at the electrode/tissue interface. U.S. Pat. No. 4,537,201 to Delle-Vedove et al. teaches a linearization of the exponentially decaying sensed signal by applying the sensed signal through an anti-logarithmic amplifier in order to detect a remaining nonlinear component caused by the evoked potential. U.S. Pat. No. 4,674,508 to DeCote, Jr. teaches the use of paired pacing pulses wherein the waveforms sensed through the pacing lead following the generation of each of the pair of pulses are electronically subtracted to yield a difference signal indicative of the evoked cardiac response. U.S. Pat. No. 4,686,988 to Sholder teaches the use of a separate sensing electrode connected to a detector for detecting P-waves in the presence of atrial stimulation pulses, wherein the P-wave detector has an input bandpass characteristic selected to pass frequencies that are associated with P-waves. U.S. Pat. No. 4,821,724 to Whigham et al. teaches the use of a triphasic stimulus having two positive pulses and one negative pulse for balancing the charge at the electrode/tissue interface. U.S. Pat. No. 4,858,610 to Callaghan et al. teaches the use of charge dumping following delivery of the stimulation pulse to decrease lead polarization and also the use of separate pacing and sensing electrodes to eliminate the polarization problem on the sensing electrode. U.S. Pat. No. 5,324,310 to Greeninger et al. teaches the use of the "ring-to-ring" sensing with corresponding atrial and ventricular EGM amplifiers whose outputs are multiplied and compared to a predetermined threshold to determine capture. U.S. Pat. No. 5,486,201 to Canfield discloses an active discharge circuit having a switching device which sequentially and repeatedly couples a charge transfer capacitor to the coupling capacitor to transfer charge therebetween and thereby actively discharge the coupling capacitor.

The foregoing prior art approaches, however, suffer from significant drawbacks. For example, the techniques of the '610 patent to Callaghan and '988 patent to Sholder, which involve using a separate electrode located at some distance from the stimulating electrode for the purpose of isolating the polarization voltages or "afterpotential," are disadvantageous in that they require the additional cost and complexity of the additional sensing electrode. The approaches of the '531 patent to Wittkampf et al. and '508 patent to DeCote, Jr. are unnecessarily wasteful of battery power and unduly complex due to the need to deliver opposite-polarity charges and pairs of closely spaced pacing pulse, respectively, to the electrode. The approach of the '201 patent to Delle-Vedove et al. is similarly disadvantageous in that it requires unnecessarily complex circuitry that it difficult to implement to produce the anti-logarithmic amplifier.

These and numerous other disadvantages of the prior art necessitates the need for the method and apparatus for automatic capture threshold detection provided by the present invention.

OBJECTS AND SUMMARY OF THE INVENTION

It is a principal object of the present invention to provide a new and improved low power consumption system for attenuating polarization voltages or "afterpotentials" at the heart tissue/electrode interface such that the evoked cardiac contractions may be readily detected.

It is a further object of the present invention to provide an improved cardiac pacemaker which minimizes the current drain to prolong the life of the battery.

In accordance with a broad aspect of the present invention, the foregoing objectives are attained by providing an improved pacing output circuit for use in a cardiac pacemaker comprising power supply means, first capacitor means, first switching means, second capacitor means, and afterpotential attenuation means. The first capacitor means is cooperatively operable with the power supply means for selectively storing a pacing charge to be delivered to myocardial tissue in a heart via an electrode. The first switching means is provided for selectively delivering the pacing charge from the first capacitor means to the myocardial tissue within the heart. The second capacitor means is coupled to the electrode and cooperatively operable with the first capacitor means for blocking DC components from the heart during pacing. The afterpotential attenuation means is provided for selectively attenuating afterpotentials which result due to the application of the pacing charge to the heart. The afterpotential attenuation means includes third capacitor means coupled to the second capacitor means and second switching means for selectively coupling the second capacitor means in series with the third capacitor means so as to reduce the effective capacitance of the second capacitor means.

In accordance with yet another broad aspect of the present invention, the foregoing objectives are attained by providing an improved method for attenuating afterpotentials in cardiac pacing systems. The improved method comprises the steps of: (a) providing an improved pacing output circuit, the pacing output circuit having means for selectively delivering a stimulating pulse to an electrode disposed within a chamber of a patient's heart and a coupling capacitor coupled to the electrode for blocking DC components from entering the patient's heart; and (b) selectively reducing the capacitance of the coupling capacitor following the application of a stimulation pulse to the patient's heart.

In accordance with a still further broad aspect of the present invention, the foregoing objectives are attained by providing an improved cardiac pacemaker comprising pulse generation means for selectively generating stimulus pulses and lead means coupled to the pulse generation means for delivering the stimulus pulses to a chamber within a patient's heart. The pulse generation means includes power supply means, first capacitor means cooperatively operable with the power supply means for selectively storing a pacing charge to be delivered to the chamber in the heart via the lead means, first switching means for selectively delivering the pacing charge from the first capacitor means to the chamber of the heart via the lead means, second capacitor means coupled to the lead means and cooperatively operable with the first capacitor means for blocking DC components from the heart during pacing, and afterpotential attenuation means for selectively attenuating afterpotentials which result due to the application of the pacing charge to the heart. The afterpotential attenuation means includes third capacitor means coupled to the second capacitor means and second switching means for selectively coupling the second capacitor means in series with the third capacitor means so as to reduce the effective capacitance of the second capacitor means.

These and further objects and advantages of the present invention will be readily apparent to those skilled in the art from a review of the following detailed description of the preferred embodiment in conjunction with the accompanying drawings and appended claims.

DESCRIPTION OF THE PREFERRED EMBODIMENT

Figure 1:
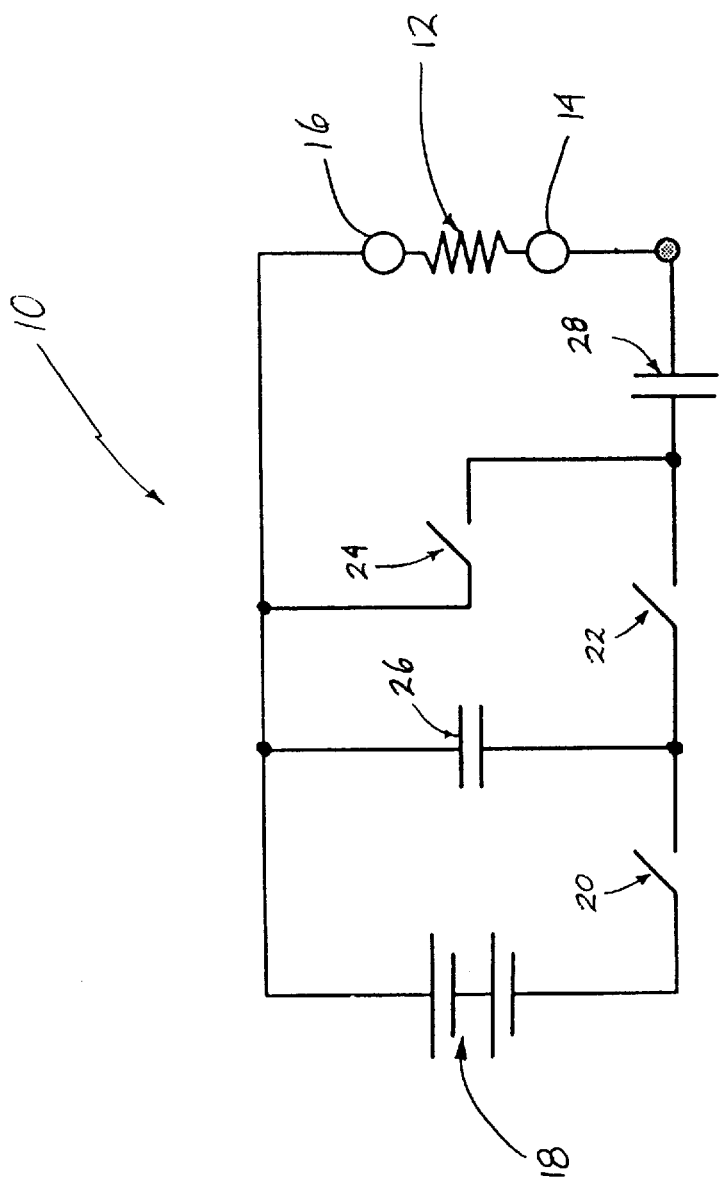
FIG. 1 is a schematic of a conventional pacing output circuit 10 employed in any of a variety of prior art cardiac pacemakers.
Figure 2:
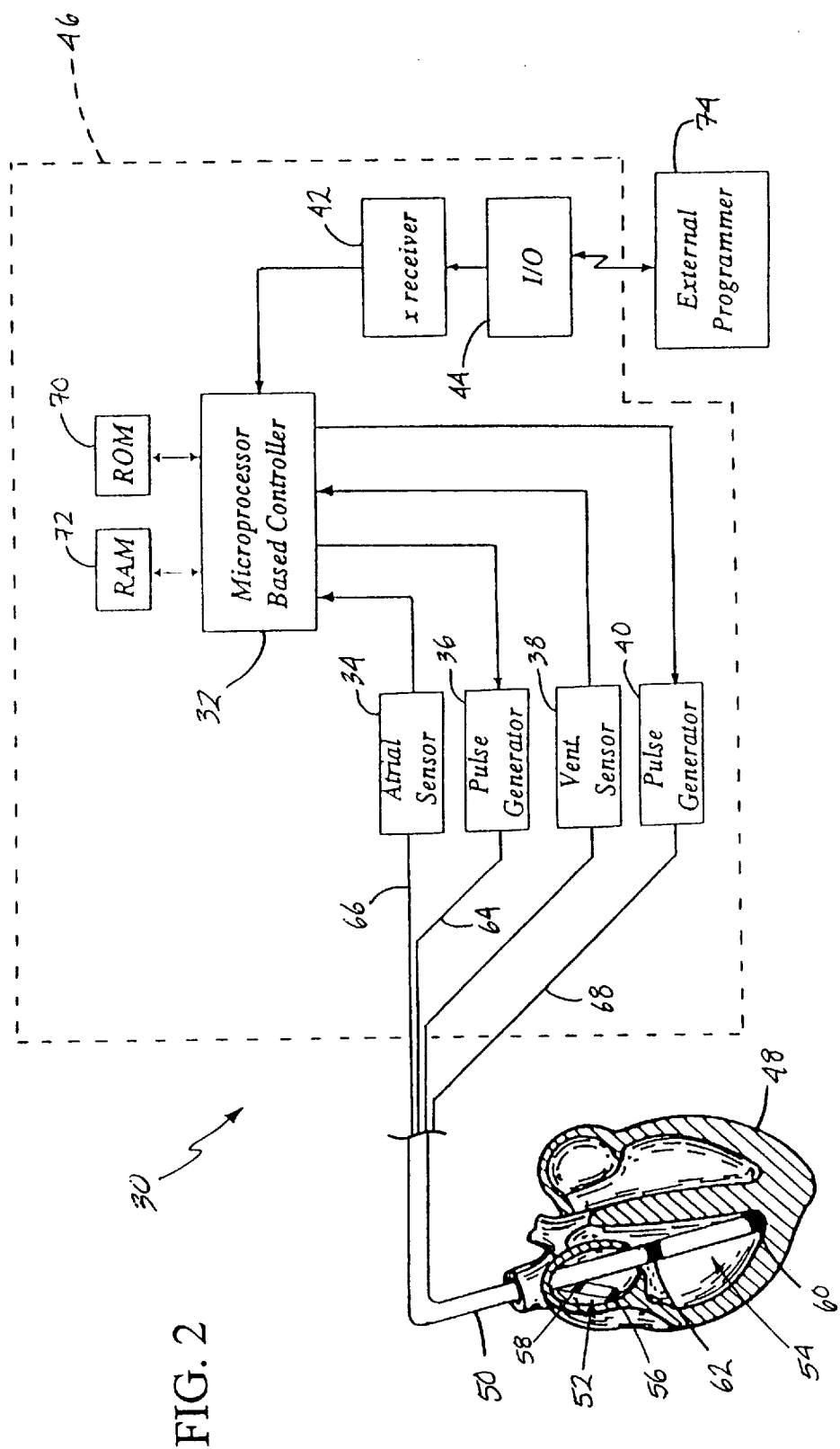
FIG. 2 is block diagram depicting a cardiac pacemaker 30 incorporating the improved pacing circuitry for automatic capture threshold detection in accordance with the present invention.

The present invention may find application in a variety of implantable or external cardiac rhythm management devices, including but not limited to bradycardia pacemakers, antitachycardia pacemakers, and defibrillators, but for purposes of explanation, will be described in connection with an implantable rate adaptive cardiac pacemaker 30 as illustrated in FIG. 2. By way of illustration and not limitation, the cardiac pacemaker 30 is a dual chamber (DDD) pacer having a microprocessor-based controller 32 operatively coupled to an atrial sense amplifier 34, an atrial pulse generator 36, a ventricular sense amplifier 38, a ventricular pulse generator 40, a transceiver 42, and an input/output module 44, all of which are disposed within a hermetically sealed housing designated schematically at 46. The cardiac pacemaker 30 is operatively coupled to a patient's heart 48 via a main pacing lead 50 which branches off into an atrial lead 52 and a ventricular lead 54. Bipolar pacing is provided, by way of example, wherein the atrial lead 52 has a tip electrode 56 and a ring electrode 58, and the ventricular lead 54 has a tip electrode 60 and a ring electrode 62. The atrial pulse generator 36 is electrically coupled to the tip electrode 56 of the atrial lead 52 via a conductor 64 for delivering stimulating pulses to the atrium under the direction of the microprocessor controller 32. The atrial sense amplifier 34 is electrically coupled to the ring electrode 58 of the atrial lead 52 via a conductor 66 for sensing the occurrence of P-wave activity relating to atrial events and forwarding this atrial information to the microprocessor controller 32. The ventricular pulse generator 40 is similarly electrically coupled to the tip electrode 60 of the ventricular lead 54 via a conductor 68 for delivering stimulus pulses to the ventricle under the direction of the microprocessor controller 32. The ventricular sense amplifier 38 is electrically coupled to the ring electrode 62 of the ventricular lead 54 for sensing the R-wave activity relating to ventricular depolarization and forwarding this ventricular information to the microprocessor controller 32. The cardiac pacemaker 30 also includes read-only memory (ROM) 70 and random access memory (RAM) 72 communicatively coupled to the microprocessor controller 32. The transceiver 42 is cooperatively operable with the input/output module 44 for transmitting and receiving information to and from an external programmer 74.

Figure 3:
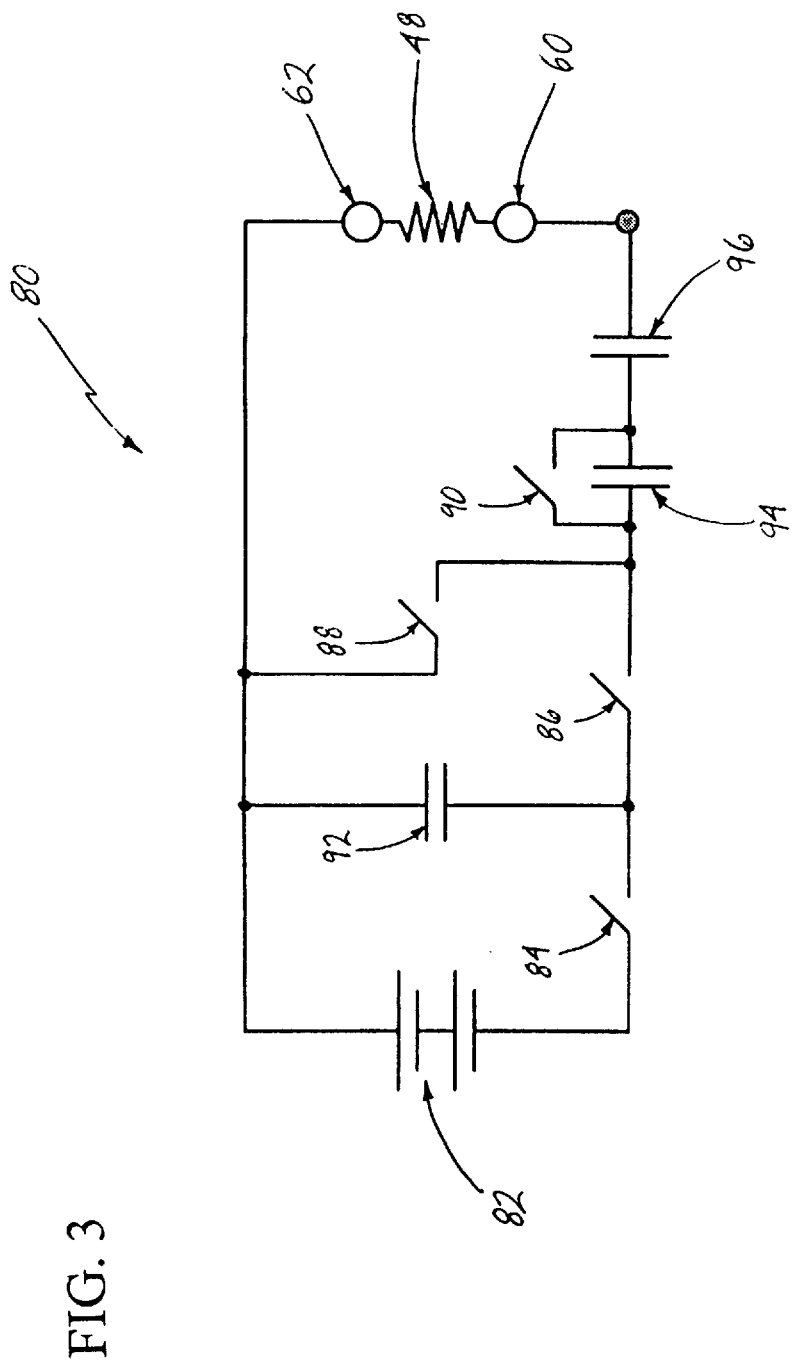
FIG. 3 is schematic of an improved pacing output circuit 80 provided in accordance with a preferred embodiment of the present invention.

With reference to FIG. 3, the present invention comprises an improved pacing output circuit 80 for use within the atrial and ventricular pulse generators 36, 40 of the pacemaker 30 shown in FIG. 2. As will be explained below, the improved pacing output circuit 80 is capable of quickly attenuating any polarization voltages or "afterpotentials" which result due to the application of stimulus pulses to the heart 48. By attenuating the polarization voltages or "afterpotentials" in this fashion, the improved pacing circuit 80 of the present invention facilitates the task of capture verification in that the presence or absence of evoked responses may be readily determined without the masking caused by afterpotentials. Capture verification advantageously allows the pacemaker 30 to automatically adjust the capture threshold so as to minimize power consumption while assuring therapeutic efficacy.

In a preferred embodiment, the improved pacing output circuit 80 of the present invention includes a power supply or battery 82, a first switch 84, a second switch 86, a third switch 88, a fourth switch 90, a pacing charge storage capacitor 92, an afterpotential reduction capacitor 94, and a coupling capacitor 96, all of which are cooperatively operable under the direction of the microprocessor-based controller 32 shown in FIG. 2. By way of example, the improved pacing output circuit 80 is illustrated in a ventricular pacing arrangement for delivering stimulus pulses to the heart 48 via the tip electrode 60 and ring electrode 62 of the ventricular pacing lead 54 shown in FIG. 2. It is to be readily understood, however, that the improved pacing output circuit 80 of the present invention may also find application in an atrial pacing arrangement. The power supply or battery 82 is preferably the battery provided to power the pacemaker 30 and may comprise any number of commercially available batteries suitable for pacing applications. The switches 84–90 are illustrated as discrete components but are preferably carried out via any number of commercially available microprocessor-directed semiconductor integrated circuit switching means. The pacing charge storage capacitor 92 may also comprise any number of commercially available storage capacitors, but is preferably provided with a capacitance in the range of 10–30 microFarads so as to develop a sufficient pacing charge for stimulating the heart 48. The primary function of the coupling capacitor 96 is to block any DC signals from reaching the heart 48 during pacing. In order to ensure this DC blocking function, the coupling capacitor 96 must have a sufficiently large capacitance ranging, for example, between 15–30 microFarads. In an important aspect of the present invention, the afterpotential reduction capacitor 94 is advantageously provided having a capacitance value substantially smaller than that of the coupling capacitor 96. As will be described in greater detail below, the afterpotential reduction capacitor 94 may be selectively shorted out, via the fourth switch 90, so as to selectively reduce the effective capacitance of the coupling capacitor 96, thereby quickly attenuating the polarization voltage or "afterpotentials" which result from pacing.

The operation of the improved pacing output circuit 80 will now be described as follows. The pacing output circuit 80 engages in a charging cycle, a pacing cycle, and a recharge cycle. The charging cycle is characterized as having the first switch 84 and fourth switch 90 in a closed state with the second switch 86 and third switch 88 in an open state. In this configuration, the pacing charge storage capacitor 92 may be charged up to a predetermined pacing voltage level, such as 3 volts. After the pacing charge storage capacitor 92 has been charged up to the predetermined pacing voltage level, the pacing cycle then operates to deliver the pacing charge from the pacing charge storage capacitor 92 to the heart 48. To accomplish this pacing cycle, the first switch 84 and third switch 88 are opened and the second switch 86 and fourth switch 90 are closed. This allows the voltage within the pacing charge storage capacitor 92 to be discharged through the coupling capacitor 96 to the tip electrode 60 of the pacemaker 30. Maintaining the fourth switch 90 in the closed position effectively shorts out the afterpotential reduction capacitor 94 such that the coupling capacitor 96 is at its full capacitance level of approximately 15–30 microFarads. This, once again, effectively blocks any DC signals from reaching the heart 48. The recharge cycle involves opening the first switch 84 and the second switch 86 while closing the third switch 88 and fourth switch 90. This allows the circuit 80 to passively recharge, such that the charge within the heart 48 is allowed to flow back into the circuit 80 to balance out. However, during this passive recharge period, the charge on the coupling capacitor 96 is such that the signal would normally exponentially decay over a relatively long period of time lasting up to 100 milliseconds. As noted above, this large "afterpotential" signal unwantedly masks out any evoked response from the heart 48. This is because the evoked responses from the heart 48 typically occur within 20 milliseconds from the delivery of the stimulus pulse and are substantially smaller in magnitude than the large "afterpotential" which would develop within the coupling capacitor 96, were it not for the present invention.

It is an important aspect of the present invention that the polarization voltages or "afterpotentials" which result from pacing quickly attenuated. This is achieved by opening the second switch 86, third switch 88, and fourth switch 90 immediately after pacing such that the afterpotential reduction capacitor 94 and coupling capacitor 96 are connected in series. The series coupling of the afterpotential reduction capacitor 94 and coupling capacitor 96 causes the overall capacitance to approximate the lower capacitance, or in other words, the capacitance of the afterpotential reduction capacitor 94. In a preferred embodiment, the afterpotential reduction capacitor 94 may be provided having a capacitance in the range of 1–2 microFarads such that, for a brief moment, the overall capacitance between the afterpotential reduction capacitor 94 and coupling capacitor 96 is approximately 1–2 microFarads. Advantageously, it has been found that reducing the overall capacitance of the coupling capacitor 96 quickly attenuates the polarization voltages or "afterpotentials" which result immediately following the application of a stimulus pulse such that the evoked responses within the heart 48 will not be masked or buried within the "afterpotential." By eliminating the adverse affects of "afterpotentials" in this fashion, the pacemaker 30 can easily determine and track the capture threshold of the heart 48 over time. With the continuous knowledge of the capture threshold in hand, the pacemaker 30 may be automatically adjusted to maintain an optimal pacing stimulus level which ensures safe pacing while minimizing power consumption.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An improved pacing output circuit for use in a cardiac pacemaker, comprising:

(a) power supply means;

(b) first capacitor means cooperatively operable with said power supply means for selectively storing a pacing charge to be delivered to myocardial tissue in a heart via an electrode;

(c) first switching means for selectively delivering said pacing charge from said first capacitor means to said myocardial tissue within said heart;

(d) second capacitor means coupled to said electrode and cooperatively operable with said first capacitor means for blocking DC components from said heart during pacing; and (e) afterpotential attenuation means for selectively attenuating afterpotentials which result due to the application of said pacing charge to said heart, said afterpotential attenuation means including third capacitor means coupled to said second capacitor means and second switching means for selectively coupling said second capacitor means in series with said third capacitor means so as to reduce the effective capacitance of said second capacitor means.

2. The improved pacing output circuit as set forth in claim 1 and further, said third capacitor means having a substantially smaller capacitance than said second capacitor means.

3. The improved pacing output circuit as set forth in claim 2 and further, said first switching means including a first switch for selectively coupling said power supply means to said first capacitor means for developing said pacing charge within said first capacitor means and a second switch for selectively coupling said first capacitor means to said second capacitor means for discharging said pacing charge from said first capacitor means into said heart via said electrode.

4. The improved pacing output circuit as set forth in claim 3 and further, said first capacitor means having a capacitance ranging from 10–40 microFarads, said second capacitor means having a capacitance ranging from 10–40 microfarads, and said third capacitor means having a capacitance ranging from 0.1–3 microfarads.

5. An improved method for attenuating afterpotentials in cardiac pacing systems, comprising the steps of:

(a) providing an improved pacing output circuit, said pacing output circuit having means for selectively delivering a stimulating pulse to an electrode disposed within a chamber of a patient's heart and a coupling capacitor coupled to said electrode for blocking DC components from entering said patient's heart; and (b) selectively reducing the capacitance of said coupling capacitor following the application of a stimulation pulse to said patient's heart.

6. An improved cardiac pacemaker, comprising:

pulse generation means for selectively generating stimulus pulses;

lead means coupled to said pulse generation means and adapted to deliver said stimulus pulses to a patient's heart;

said pulse generation means including power supply means, first capacitor means cooperatively operable with said power supply means for selectively storing a pacing charge to be delivered to said heart via said lead means, first switching means for selectively delivering said pacing charge from said first capacitor means to said heart via said lead means, second capacitor means coupled to said lead means and cooperatively operable with said first capacitor means for blocking DC components from said heart during pacing, and afterpotential attenuation means for selectively attenuating afterpotentials which result due to the application of said pacing charge to said heart; and said afterpotential attenuation means including third capacitor means coupled to said second capacitor means and a second switching means for selectively coupling said second capacitor means in series with said third capacitor means so as to reduce the effective capacitance of said second capacitor means.

7. The improved cardiac pacemaker as set forth in claim 6 and further, said third capacitor means having a substantially smaller capacitance than said second capacitor means.

8. The improved cardiac pacemaker as set forth in claim 7 and further, said first switching means including a first switch for selectively coupling said power supply means to said first capacitor means for developing said pacing charge within said first capacitor means and a second switch for selectively coupling said first capacitor means to said second capacitor means for discharging said pacing charge from said first capacitor means into said heart via said electrode.

9. The improved cardiac pacemaker as set forth in claim 8 and further, said first capacitor means having a capacitance ranging from 10–40 microFarads, said second capacitor means having a capacitance ranging from 10–40 microfarads, and said third capacitor means having a capacitance ranging from 0.1–3 microfarads.

\* \* \* \* \*